Figure 1:
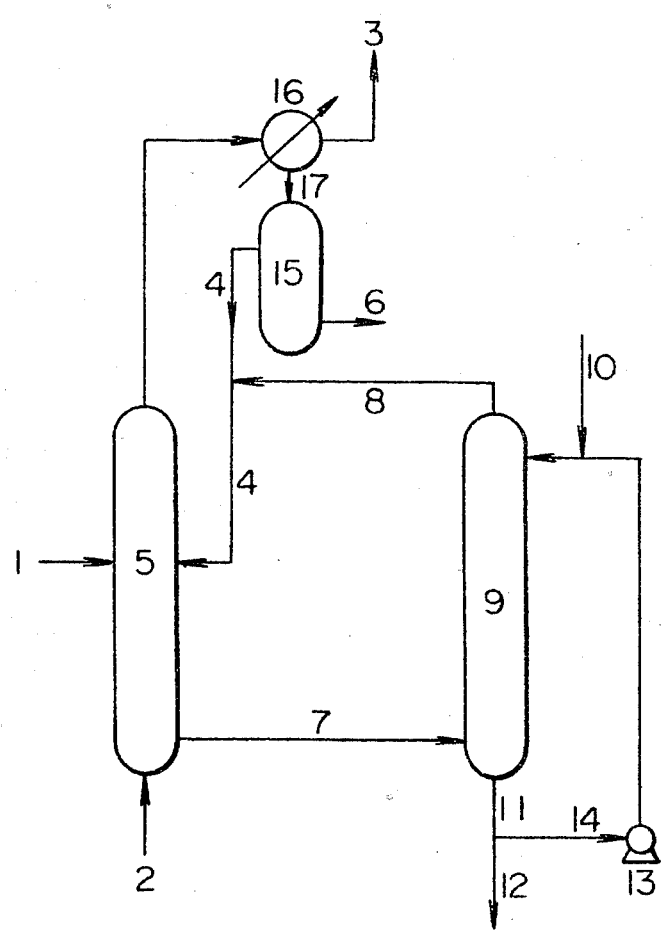

United States Patent [19]
Fujita et al.

[11] 3,991,099
[45] Nov. 9, 1976

[54] PROCESS FOR THE PREPARATION OF MIXTURE CONSISTING PREDOMINANTLY OF ε-HYDROXYCAPROIC ACID, ADIPIC ACID, α-FORMYLVALERIC ACID AND THE ESTERS OF THESE ACIDS

[75] Inventors: Yutaka Fujita; Koji Nakagawa; Yuitsu Honda, all of Iwakuni, Japan

[73] Assignee: Teijin Limited, Osaka, Japan

[22] Filed: Dec. 28, 1973

[21] Appl. No.: 429,182

Related U.S. Application Data

[63] Continuation of Ser. No. 200,703, Nov. 22, 1971, abandoned.

[30] Foreign Application Priority Data

July 28, 1971 Japan.............................. 46-56489

[52] U.S. Cl. ............................ 260/483; 260/535 R; 260/533 C; 260/343; 260/537 P; 260/531 R; 260/485 R; 260/484 R
[51] Int. Cl.$^2$.................. C07C 59/04; C07C 51/18; C07C 67/42
[58] Field of Search ........ 260/531 R, 533 C, 535 R, 260/537 P, 483, 484 R, 485 R

[56] References Cited
FOREIGN PATENTS OR APPLICATIONS
935,029   8/1963   United Kingdom............. 260/531 R Primary Examiner—Anton H. Sutto
Assistant Examiner—Richard D. Kelly
Attorney, Agent, or Firm—Sherman & Shalloway

[57] ABSTRACT

A process for preparing a mixture of organic carboxylic acids and esters thereof consisting predominantly of epsilon-hydroxycaproic acid, adipic acid, formylvaleric acid, and esters of these acids by oxidizing a mixture of cyclohexane, cyclohexanol and cyclohexanone with molecular oxygen, which comprises withdrawing at least a part of the oxidation reaction mixture from the oxidation reaction system, extracting the organic carboxylic acids and esters thereof from the oxidation reaction mixture until the concentration of the total carboxyl groups of said oxidation reaction mixture is reduced to a value not greater than 1.2 gram equivalents per liter of the reaction mixture, the several ester bonds of the esters contained in reaction mixture being considered to be carboxyl groups, recycling to the oxidation reaction system the resulting liquid extraction residue containing unreacted cyclohexane, cyclohexanol and cyclohexanone and carrying out the oxidation reaction, while recovering the carboxylic acids and esters thereof from the liquid extract.

5 Claims, 3 Drawing Figures

PROCESS FOR THE PREPARATION OF MIXTURE CONSISTING PREDOMINANTLY OF ε-HYDROXYCAPROIC ACID, ADIPIC ACID, α-FORMYLVALERIC ACID AND THE ESTERS OF THESE ACIDS

This is a continuation of application Ser. No. 200,703, filed Nov. 22, 1971 now abandoned.

This invention relates to a process for the preparation of a mixture consisting predominantly of epsilon-hydroxycaproic acid, adipic acid, delta-formylvaleric acid and esters of these acids by oxidizing a liquid mixture of cyclohexane, cyclohexanol and cyclohexanone with molecular oxygen.

More particularly, the invention relates to a process which comprises oxidizing a liquid mixture of cyclohexane, cyclohexanol and cyclohexanone with molecular oxygen, extracting and separating from the so oxidized reaction mixture the organic carboxylic acids such as epsilon-hydroxycaproic acid, adipic acid and delta-formylvaleric acid and the esters of these organic carboxylic acids, which have been formed by the foregoing oxidation reaction, followed by recycling to the aforesaid oxidation reaction system the liquid extraction residue containing unreacted cyclohexane, cyclohexanol and cyclohexanone to effect their reoxidation and, at the same time, recovering the aforesaid organic carboxylic acids and esters thereof from the liquid extract.

As a method of preparing epsilon-hydroxycaproic acid by oxidizing a liquid mixture consisting of cyclohexane, cyclohexanol and cyclohexanone (for convenience hereinafter referred to as cyclohexane mixture) with molecular oxygen, that disclosed in British Pat,. No. 935,029 has been known. This method comprises oxidizing the aforesaid cyclohexane mixture with molecular oxygen, continuously withdrawing from the oxidation reaction system, the reaction mixture in which epsilon-hydroxycaproic acid has been formed, contacting the withdrawn oxidation reaction mixture with a ¼ – 5-fold amount of water to extract the epsilon-hydroxycaproic acid in the foregoing water phase, and recycling the remaining cyclohexane, cyclohexanol and cyclohexanone to the oxidation reaction system.

However, according to studies, it has been found that the selectivity for epsilon-hydroxycaproic acid which forms by the oxidation reaction gradually declines when the oxidation method of the British patent is carried out over a prolonged period of time and that there is a concomitant increase in the amount of by-products formed in the form of oxides of high order whose structure is not clear. Accordingly, it was found that it was impossible to continue the foregoing oxidation reaction while maintaining a satisfactory selectivity for the epsilon-hydroxycaproic acid.

As a result of having inquired into the cause for this gradual decline in the selectivity for epsilon-hydroxycaproic acid as the reaction proceeds in the aforesaid oxidation reaction wherein oxidizing the cyclohexane mixture with molecular oxygen the epsilon-hydroxycaproic acid formed is extracted from the reaction mixture with water and thereafter the liquid residue containing the unreacted cyclohexane, cyclohexanol and cyclohexanone is recycled to the reaction system, we found that the principal cause was due to the fact that there were recycled to the oxidation reaction system by entrainment in the cyclohexane, cyclohexanol and cyclohexanone those organic carboxylic acids and esters thereof which were not extracted during the water extraction of the oxidation reaction mixture, and that as the concentration of these organic carboxylic acids and their esters increased in the oxidation reaction system, the selectivity for epsilon-hydroxycaproic acid in particular declined.

When a mixture of cyclohexane, cyclohexanol and cyclohexanone is oxidized with milecular oxygen, e.g. air, the various organic carboxylic acids, such as indicated below, are formed as the principal carboxylic acids; for example:

Epsilon-hydroxycaproic acid (HO-$(CH_2)_5$-COOH)
Adipic acid (HOOC-$(CH_2)_4$-COOH)
Delta-formylvaleric acid (OHC-$(CH_2)_4$-COOH).

In addition, a small amount of other organic carboxylic acids, such as indicated below, is formed; for example:
Glutaric acid
Succinic acid
5-Hydroxycaproic acid
4-Hydroxyvaleric acid
Acetic acid
Butyric acid
Valeric acid
Caproic acid
Cyclohexylhydroxycaproic acid.

Of these organic carboxylic acids, epsilon-hydroxycaproic acid which is a compound that is especially self-condensable, forms low polyconsensation products thereof. Further, epsilon-hydroxycaproic acid and/or its low polycondensation products form a wide variety of esters with one or more of the various organic carboxylic acids indicated above such as adipic acid, delta-formylvaleric acid and the other carboxylic acids indicated above, as well as with cyclohexanol.

Again, epilon-caprolactone, an ester inside the epsilon-hydroxycaproic acid molecule, also forms as a result of the foregoing oxidation reaction. Therefore, for convenience the low polycondensation products of epsilon-hydroxycaproic acid and the various esters hereinabove described inclusive of epsilon-caprolactone, will be referred to herein merely as esters.

ONE EXAMPLE OF AN APPARATUS FOR PRODUCING THE PRESENT INVENTION

The present invention will be described below with reference to the accompanying drawings.

FIG. 1 is a flow chart which illustrates the principal parts of one example of an oxidation apparatus which can be used for carrying out the invention.

In FIG. 1, 5 is a cyclohexane oxidation tower and 9 is a extraction tower for the carboxylic acids formed. Cyclohexane is introduced to the oxidation tower 5 via line 1 while molecular oxygen, e.g. air, is introduced to the bottom of the oxidation tower 5 via line 2. The exhaust gas from the oxidation tower enters a cooler-condenser 16, and the condensed component enters a decanter 15 via line 17. The water separated by the decanter is withdrawn via line 6 while, on the other hand, the unreacted cyclohexane is returned to the oxidation tower 5 via line 4. The reaction mixture is conducted from the oxidation tower via line 7 to the extraction tower 9. On the other band, an extraction agent is introduced via line 10 to the extraction tower 9, where it is brought into contact with the reaction mixture. The liquid extraction residue containing the unreacted cyclohexane, cyclohexanol and cyclohexanone is withdrawn from the extraction tower 9 and returned via line 8 to the oxidation tower 5. The liquid extract is withdrawn via lines 11 and 12, while a part thereof is recycled by means of a pump 13 to the extraction tower 9 via line 14. A fresh supply of the extraction agent in an amount equivalent to that withdrawn via line 12 is added to the extraction tower 9 via line 10. Further, the reaction mixture in the oxidation tower 5 is held at a constant level by feeding cyclohexane thereto constantly in a suitable amount.

THE DRAWBACKS OF THE CONVENTIONAL PROCESS

The foregoing apparatus shown in FIG. 1 was used, but, by way of comparison, the oxidation rection was carried out in the following manner. Water was constantly fed into the extraction tower 9 via line 10 in an amount of ½-fold (volume) the liquid amount of the oxidation reaction product introduced to the extraction tower 9 via line 7, followed by withdrawing the liquid extract via line 11 provided at the bottom of the extraction tower 9. On the other hand, the liquid extraction residue (containing the unreacted cyclohexane, cyclohexanol and cyclohexanone) was recycled to the oxidation tower 5 via lines 8 and 4, while cyclohexane was introduced to the oxidation tower via line 1 to maintain the liquid content in the oxidation tower 5 at a constant level. The reaction was continued in this manner for 300 hours, with the consequence that the results shown in FIG. 2 were obtained. The particulars of the reaction conditions in this case were as follows:

| | |
|---|---|
| Reaction temperature inside the reaction tower 5 | 140° C. |
| Reaction pressure inside the reaction tower 5 | 7 kg/cm$^2$G |
| Average residence time in the reaction tower 5 | 0.6 hr. |
| Amount of the oxidation reaction mixture withdrawn via line 7 | 18.3 vol parts/hr. |
| Temperature of extraction tower | 80° C. |
| Amount of water introduced via line 10 | 9.15 vol parts/hr. |
| Amount of the liquid extract withdrawn via line 12 | 9.2 vol parts/hr. |
| Concentration of total carboxyl withdrawn via line 12 | 0.36g equiv/liter |

Figure 2:
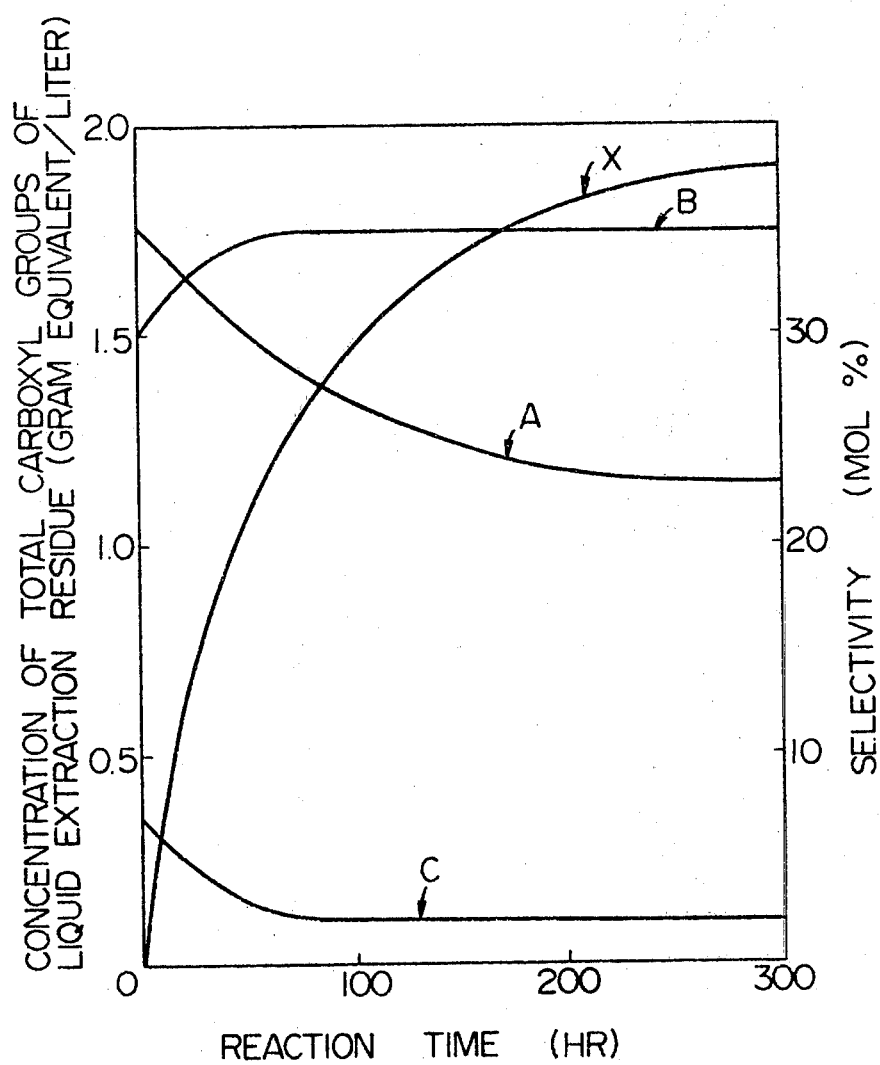

In FIG. 2 the abscissa is the number of hours the aforesaid oxidation reaction was continued, while the ordinate at the left is the concentration of the total carboxyl groups of the liquid extraction residue recycled to the oxidation tower 5 (gram equivalent per liter of the reaction solution) and the ordinate at the right is the rate of selectivity (mol %) for epsilon-hydroxycaproic acid, adipic acid and delta-formylvaleric acid, which are recovered from the liquid extract. The curve X in this figure represents the change in the concentration of the total carboxyl groups of the liquid extraction residue that takes place as the reaction time increases (see the left side ordinate axis). Curves A, B and C represent the changes that take place in the rates of selectivity for epsilon-hydroxycaproic acid, adipic acid and delta-formylvaleric acid, respectively, as the oxidation reaction time increases (see the right side ordinate axis).

The foregoing terminology "the concentration of the total carboxyl groups in the liquid extraction residue" is a value expressed in gram equivalents per liter of liquid extraction residue of the concentration of the total carboxyl groups of the liquid extraction residue when the several ester bonds of the esters contained therein are considered as being carboxyl groups. The terminology "the concentration of the total carboxyl groups" or merely "the concentration of carboxyl groups", as used herein, is understood as being used in accordance with the foregoing definition. Further, the same definition is also applicable herein with respect to the concentration of the total carboxyl groups of the extraction agent or the oxidation reaction mixture.

This concentration of the total carboxyl groups (gram equivalent/liter) is determined in the following manner. For example, a prescribed amount (e.g. 10 ml) of the liquid extraction residue or oxidation reaction mixture is taken, following which a prescribed amount of an ethanol solution of caustic soda of known concentration (e.g. 50 ml of 1 normal NaOH ethanol solution) is added thereto. This is followed by heating and saponifying this mixture and thereafter titrating by neutralizing the remaining amount of caustic soda with an aqueous hydrochloric acid solution of known concentration (e.g. 1 normal HCl aqueous solution). Now, using, for example, those illustrated in the foregoing parentheses and assuming that the amount of the 1 normal hydrochloric acid aqueous solution was, 35 ml, for example then $$\frac{50-35}{10} = 1.5.$$

Thus, the concentration of the total carboxyl groups becomes 1.5 gram equivalents per liter of the aforesaid liquid extraction residue or reaction mixture.

Since the peroxides in the sample of the liquid extraction residue or reaction mixture become a hindrance in carrying out actual titration, the analytical operation was carried out after the catalytic hydrogenation of the peroxides in the presence of a noble metal catalyst, e.g. platinum.

As is apparent from the curve X of FIG. 2, the concentration of the total carboxyl groups in the liquid extraction residue that is recycled from the extraction tower 9 to the oxidation tower 5 gradually increases with the continuance of the oxidation reaction, and in concomitance therewith a considerably greater decline in the selectivity for c-hydroxycaproic acid (see curve A) takes place.

Thus, it is apparent from the results shown in FIG. 2 that when the oxidation reaction is carried out by extracting the oxidation reaction mixture with about a ½-fold amount of water while recycling the resulting liquid extraction residue to the oxidation reaction system, the concentration of the total carboxyl groups in the reaction mixture in the oxidation reaction system gradually increases and, in concomitance therewith, the selectivity for epsilon-hydroxycaproic acid declines, with the consequence that the overall selectivity for epsilon-hydroxycaproic acid, adipic acid, delta-formylvaleric acid, and the esters thereof also inevitably declines.

The rates of selectivity for epsilon-hydroxycaproic acid, adipic acid and delta-formylvaleric acid of FIG. 2 were determined in the following manner.

Selectivity for epsilon-hydroxycaproic acid $$\frac{\text{Number of moles of } \epsilon\text{-hydroxycaproic acid in 1 liter of the extractant}}{\text{Number of moles of total carboxylic acids in 1 liter of the extractant}} \times 100 \, (\%)$$

Selectivity for adipic acid $$\frac{\text{Number of moles of adipic acid in 1 liter of the extractant}}{\text{Number of moles of total carboxylic acids in 1 liter of the extractant}} \times 100 \, (\%)$$

Selectivity for delta-formylvaleric acid $$\frac{\text{Number of moles of } \delta\text{-formylvaleric acid in 1 liter of the extractant}}{\text{Number of moles of total carboxylic acids in 1 liter of the extractant}} \times 100 \, (\%)$$

The cuantitative determination of epsilon-hydroxycaproic acid and adipic acid for making the foregoing calculations was carried out in the following manner. After adding caustic soda to a given quantity of the extractant phase to saponify, it was acidified with hydrochloric acid and extracted with ether, followed by methyl caterification thereof by the addition of an ether solution of diazomethane to convert it into methyl adipate and methyl epsilon-hydroxycaproate, which were then measured by gas chromatography. On the other hand, in the quantitative determination of delta-formylvaleric acid, a given amount of the extructant phase is acidified with hydrochloric acid and extracted with ether after which this is converted to a methyl ester by the addition of an ether solution of diazomethane, and thereafter the resulting methyl delta-formylvalerate is measured by gas chromatography. The amount of the total carboxylic acids in the extractant is determined in the following manner. Saponification of a given amount of the extractant phase is carried out by adding caustic soda, after which the number of gran equivalents of carboxylic acids is obtained by potentiometric titration, and thereafter the number of moles of adipic, glutaric and succinic acids present in the extractant phase is substracted from the value obtained by potentiometric titration. The so obtained value is the number of moles of total carboxylic acids.

As is apparent from the results shown in FIG. 2, the preparation of the organic carboxylic acids and the esters thereof, as intended by the present invention, while maintaining a high selectivity for these acids and esters is not possible by the method wherein the aforesaid reaction mixture is merely extracted with water in an amount on the order of ½-fold based on the reaction mixture, followed by recycling the liquid extraction residue to the oxidation reaction system. On the other hand, when the amount of the extraction water is increased beyond the foregoing figure, the separation and recovery of the intended organic carboxylic acids and esters thereof from the liquid extract not only becomes difficult, but also greater expense will be required.

FEATURES OF THE PRESENT INVENTION

However, according to our studies it has been found that in the process for preparing a mixture of organic carboxylic acids and esters thereof consisting predominantly of epsilon-hydroxycaproic acid, adipic acid, formylvaleric acid and the esters of these acids by oxidizing cyclohexane, cyclohexanol and cyclohexanone with molecular oxygen, it is possible to prepare the foregoing mixture while maintaining a high selectivity by a method comprising withdrawing at least a part of the oxidation reaction mixture from the oxidation reaction system, extracting the aforesaid organic carboxylic acids and estera thereof from the oxidation reaction mixture until the carboxyl group concentration is reduced to a value not greater than 1.2 gram equivalents, and preferably not greater than 0.7 gram equivalent, per liter of the oxidation reaction mixture with the several ester bonds in the case of esters being considered carboxyl groups, recycling to the aforesaid oxidation reaction system the resulting liquid extraction residue containing unreacted cyclohexane, cyclohexanol and cyclohexanone and carrying out the oxidation reaction, while recovering the aforesaid organic carboxylic acids and esters thereof from the liquid extract.

According to the invention, any extraction method may be used for reducing the concentration of the total carboxyl groups of the liquid extraction residue to be recycled to the oxidation reaction system to a value not greater than 1.2 gram equivalents, preferably not greater than 0.7 gram equivalent, per liter of the liquid extraction residue.

EXTRACTION OPERATION (1) OF THE INVENTION

According to research it has been discovered that for reducing the concentration of the total carboxyl groups in the liquid extraction residue to be recycled to the oxidation reaction system to a concentration below that indicated above, a method, wherein the foregoing oxidation reaction mixture is contacted with an aqueous solution containing the organic carboxylic acids and esters thereof to be formed by the oxidation reaction, in terms of the concentration of the total carboxyl groups, in an amount of 4 gram equivalents per liter to 7 gram equivalents per liter, with the several ester bonds in the case of the esters being considered to be carboxyl groups, is very effective in accomplishing the extraction of the organic carboxylic acids and esters thereof from the oxidation reaction mixture. It was a great surprise to find that in extracting and separating the organic carboxylic acids and esters thereof from the oxidation reaction mixture, the use of an aqueous solution in which a large amount of the same organic carboxylic acids and their esters is dissolved could very effectively extract the organic carboxylic acids and esters thereof that were contained in the reaction mixture. In carrying out this extraction, the temperature preferably used is one in the range of 40°–150° C., and especially 50°–100° C. By carrying out the extraction at such a temperature, not only can the extraction agent be maintained in its liquid state but also the extraction effects can be enhanced.

When an aqueous solution in which the organic carboxylic acids and esters thereof that are formed by the oxidation reaction of the are dissolved is used as the extraction agent in accordance with the hereinabove described extraction method, the concentration of the total carboxyl groups of this extraction agent can be determined by the same method of analysis as previously described with reference to FIG. 2.

Further, in this extraction operation, the oxidation reaction mixture need not be contacted from the outset with an equeous solution whose concentration of the total carboxyl groups is 4 gram equivalents per liter to 7 gram equivalents per liter as long as the contact of the oxidation reaction mixture is made with an aqueous solution having the foregoing concentration of the total carboxyl groups is carried out during at least one period of the extraction operation. For example, an instanse where a multitray extraction tower is used without using a pump to carry out the circulation will be described with reference to FIG. 1. Now, if, as compared with the amount of the liquid oxidation reaction on mixture introduced via line 10 to the extraction tower 9, a considerably small amount of water, e.g. one-tenth volume of water, is fed from the top of the extraction tower, the organic carboxylic acids in the reaction mixture are first extracted into the water and the concentration of the organic carboxylic acids in the water gradually increases, and in concomitance with this increase in concentration of the organic carboxylic acid, the amount of the esters distributed in reaction mixture increases. Thus, as the relatively small amount of water fed at the top of the extraction tower 9 flows down from the top of the tower to its bottom, a gradual increase takes place in the amount of the organic carboxylic acids and esters thereof that are in solution in the water. Therefore, the concentration of the total carboxyl groups of the organic carboxylic acids and esters thereof of the aqueous solution becomes at least 4 gram equivalents per liter, with the consequence that the reaction mixture introduced from the bottom of the extraction tower makes contact with an aqueous solution of this concentration making it possible to extract the organic carboxylic acids and esters thereof that are contained in the reaction mixture. Therefore, in accordance with the invention, an aqueous solution, as hereinabove indicated, in which the concentration of the total carboxyl groups of the organic carboxylic acids and esters thereof is less than 4 gram equivalents per liter may be fed to the top of the extraction tower 9 in carrying out the extraction operation.

To ensure that a thorough contact is had between the oxidation reaction mixture and the aqueous solution of organic carboxylic acids and esters of a concentration of the total carboxyl groups of 4 gram equivalents to 7 gram equivalents per liter, as hereinabove indicated, while using water in carrying out the extraction, the amount of water used is influenced by the rate of conversion of the oxidation reaction products, but a suitable range is 1/30 –1/5 parts by volume based or the oxidation reaction mixture. When the rate of conversion is low, the amount of water can usually be reduced, whereas when the conversion is high, the amount can be increased.

When, in accordance with the invention, the extraction of the oxidation reaction mixture is carried out using an aqueous solution containing at a high concentration the organic carboxylic acids and esters thereof that are formed by the invention oxidation reaction, not only can the organic carboxylic acids contained in the reaction mixture extracted but especially the esters of organic carboxylic acids contained therein can also be extracted exceedingly well. Therefore, it becomes possible to reduce the concentration of the total carboxyl groups of the liquid extraction residue (containing unreacted cyclohexane, cyclohexanol and cyclohexanone) to below 1.2 gram equivalents per liter, as intended by the invention, with the consequence that even though this liquid extraction residue is recycled to the oxidation reaction system, the concentration of the total carboxyl groups of the reaction mixture in the oxidation reaction system can be controlled at a low concentration.

Thus, a mixture predominantly of epsilon-hydroxycaproic acid, adiptic acid, delta-formylvaleric acid and the esters of these acids can be prepared while maintaining a high selectivity according to the present invention. Furthermore, since these intended organic carboxylic acids and esters thereof are extracted as an aqueous solution of very high concentration, the operation of separating these intended organic carboxylic acids and esters is facilitated.

EXTRACTION OPERATION (2) OF THE INVENTION

A. As is apparent from the foregoing description, a feature of this invention resides in the fact that in practicing the oxidation reaction the concentration of the total carboxyl groups attributable to the organic carboxylic acids and their esters of the reaction mixture in the oxidation reaction system is held at as low a value as possible. For accomplishing this, it is important to ensure that the concentration of the total carboxyl groups contained in the liquid extraction residure that is recycled to the oxidation reaction system is held to below 1.2 gram equivalents per liter.

For achieving this end, it is possible according to the invention to bring into contact the aforesaid oxidation reaction mixture and as an extraction agent water or an aqueous solution containing the foregoing carboxylic acids and/or esters thereof at a concentration of the total carboxylic groups of not greater than 7 gram equivalents per liter to thereby extract into the foregoing extraction agent the carboxylic acids and esters thereof that are contained in the oxidation reaction mixture and reduce the concentration of the total carboxyl groups in the liquid extraction residue to below 1.2 gram equivalents per liter, following which a part of the liquid extraction residue, and preferably 1–5% by weight thereof, is withdrawn externally of the system and the remaining part of the liquid extraction residue, i.e., 99–95% by weight thereof, is recycled to the oxidation reaction system. Thus, it is possible to reduce the concentration of the total carboxyl groups of the reaction mixture in the oxidation reaction system to a desirably lower concentration by just the withdrawal of only a minor part of the liquid extraction residue externally of the system. On the other hand, that part of the liquid extraction residue withdrawn externally of the oxidation reaction system is submitted to distilltion to separate the cyclohexane, cyclohexanol and cyclohexanone contained therein, which are returned to the oxidation reaction system. Since the residue contains the intended organic carboxylic acids and the esters thereof, the final products may be recovered from this residue, or this residue may be used as the extraction agent after combining with the aforesaid liquid extraction residue.

B. Further, in accordance with the invention, an aqueous solution in which the organic carboxylic acids and esters thereof that are formed by the invention oxidation reaction, are dissolved the concentration of which in terms of the concentration of the total carboxyl groups is from 4 gram equivalents per liter to 7 gram equivalents per liter, can be used as the extraction agent. In this case, by following the procedure described in connection with the foregoing extraction operation (1), the oxidation reaction mixture is contacted with the foregoing extraction agent, whereby the organic carboxylic acids and esters thereof that are contained in the oxidation reaction mixture are extracted into the extracting agent. The liquid extraction residue that is obtained in the above procedure can then be again extracted by being contacted with water or an aqueous solution containing the organic carboxylic acids and esters thereof at a low concentration of 0–1.5 gram equivalents per liter, followed by recycling this liquid extraction residue to the oxidation reaction system. By carrying out this two-stage extraction operation, and especially the latter stage extraction operation, the amount of the organic carboxylic acids contained in the liquid extraction residue recycled to the oxidation reaction system is further reduced and, as a consequence, the concentration of the total carboxyl groups is reduced to that extent, and in concomitance therewith the selectivity for the formation of epsilon-hydroxycaproic acid by the oxidation reaction is further enhanced (see curve A of FIG. 2).

EXTRACTION OPERATION (3) OF THE INVENTION

Further, in accordance with the invention, at least one glycol selected from the group consisting of 1,2-propanediol, 1,4-butanediol, 1,5-pentanediol, 1,6-hexanediol and diethylene glycol can be used as the extraction agent to extract the aforesaid oxidation reaction mixture, following which the resulting liquid extraction residue is reduced in its concentration of the total carboxyl groups to below 1.2 gram equivalents, and preferably 0.7 gram equivalent per liter, and recycled wholly or partly to the aforesaid oxidation reaction system.

In this case, the foregoing glycols may be an aqueous solution containing as a whole less than 50% by weight of water. When such an extraction agent is used in a relatively small amount, the effect of extracting the aforesaid organic carboxylic acids and esters thereof is further enhanced when an aqueous glycol solution of 20–30% by weight of water content is used when compared with the case of the use of the glycol alone.

However, when the foregoing glycols or an aqueous solution thereof have been used, it is not desirable that the glycol be present in the liquid extraction residue which is to be recycled to the oxidation reaction system. Therefore, the liquid extraction residue obtained after extracting the oxidation reaction mixture with the foregoing glycols or an aqueous solution thereof is preferably treated to remove its glycol content by further washing with, for example, water.

Of the foregoing glycols, 1.6-hexanediol is especially preferred for use as the extraction gent. The reason is because 1,6-hexanediol is the most effective agent for extracting the organic carboxylic acids and esters thereof, as can be seen from Table 1, below. Moreover, when the 1,6-hexanediol containing the aforesaid organic carboxylic acids and esters thereof is directly, or after its reduction, heated at reduced pressure under conditions such as makes possible the distillation of epsilon-caprolactone, the formation of epsilon-caprolactone can be carried out in a single step.

Table 1

DISTRIBUTION COEFFICIENTS OF THE ORGANIC CARBOXYLIC ACIDS AND ESTERS FORMED BY THE INVENTION OXIDATION REACTION

| Class of Extraction Agent | Distribution Coefficient |
| --- | --- |
| 1,4-butanediol | 2.36 |
| 1,2-propanediol | 2.55 |

Table 1-continued

DISTRIBUTION COEFFICIENTS OF THE ORGANIC CARBOXYLIC ACIDS AND ESTERS FORMED BY THE INVENTION OXIDATION REACTION

| Class of Extraction Agent | Distribution Coefficient |
| --- | --- |
| diethylene glycol | 2.62 |
| 1,5-pentanediol | 2.85 |
| 1,6-hexanediol | 3.14 |

The distribution coefficients in the above table were values obtained by means of the following equation.

$$\text{Distribution coefficient} = \frac{\text{Number of gram equivalents of the total carboxyl groups per unit weight of the extraction solution}}{\text{Number of gram equivalents of the total carboxyl groups per unit weight of the liquid extraction residue}}$$

Further, in determining the foregoing distribution coefficients, measurements of "the organic carboxylic acids and esters formed by the oxidation reaction" were made using the liquid extraction residues obtained in the hereinafter given Control I.

OXIDATION CONDITIONS OF THE INVENTION

According to the invention, in preparing the foregoing carboxylic acids consisting predominantly of epsilon-hydroxycaproic acid, adipic acid and delta-formylvaleric acid and one or more of the esters thereof by oxidizing a liquid mixture of cyclohexane, cyclohexanol and cyclohexanone by contacting such a mixture with either molecular oxygen or a molecular oxygen-containing gas, any of the known conditions may be employed. Such oxidation conditions are disclosed, for example, in British patent specification No. 935,029, U.S. Pat. No. 3,515,751, German Pat. No. 1,216,284 and U.S. Pat. No. 3.390,174.

However, it was found according to studies that the oxidation reaction is preferably carried out by contacting the liquid mixture of cyclohexane, cyclohexanol and cyclohexanone with either molecular oxygen or a molecular oxygen-containing gas, e.g., air at a temperature in the range of 120°–150° C. and a pressure in the range of 3–30 atmospheres. It was further found that by preferably carrying out the oxidation reaction such that the overall water content of the oxidation reaction mixture does not exceed 1% by weight and moreover such that the conversion of cyclohexane does not exceed 4.5 mol %, and perferably such that it is 1–4 mol %, and by extracting the oxidation reaction mixture by the hereinbefore described invention method and thereafter recycling the liquid extraction residue, as described, the foregoing organic carboxylic acids and esters thereof could be prepared while maintainig a high selectivity for an exceedingly long period of time. Further, the absence from the foregoing oxidation reaction of the known oxidation catalysts such, for example, as the cobalt, manganese, iron, chromium, nickel and copper salts of such acids as naphthenic or stearic acid is preferred.

The organic carboxylic acids consisting predominantly of epsilon-hydroxycaproic acid, adipic acid and delta-formylvaleric acid and one or more of the esters of these organic carboxylic acids thus prepared by the invention process can then be submitted to a step of hydrolyzing the esters, if necesary after which the foregoing acids can be separated, and recovered. On the other hand, if the mixture of the foregoing acids and the esters is hydrogenated in the presence of 1.6-hexanediol, epsilon-hydroxycaproic acid and its low polymer are obtained as the principal products. Again, if the aforesaid mixture of organic acids and esters or the hydrogenated product thereof is heated under conditions such as makes possible the distillation of epsilon-caprolactone at reduced pressure in the presence of a suitable amount of an alcoholic hydroxyl group-containing compound, the mixture or the epsilon-hydroxycaproic acid, the low polymers thereof and esters thereof are converted to epsilon-caprolactone, which can be readily converted to epsilon-caprolactam by reacting it with ammonia.

For the foregoing reason, the aforesaid mixture of organic carboxylic acids and esters thereof is not only important in that the several carboxylic acids can be separated and obtained therefrom but also is very valuable commercially as in intermediate in its as-obtained state.

The following examples are given for further illustration of the invention. It is to be understood, however, that these examples are given to facilitate a better understanding of the invention and not to be construed as limiting the invention in and way whatsoever.

Experiment A

Experiment A illustrates one specific mode of practicing the invention.

EXAMPLE I

Example I will be described with reference to FIG. 1.

Cyclohexane was fed via line 1 to an 11-liter stainless steel bubbling column type reaction tower 5 maintained at a pressure of 7 kg/cm$^2$ gauge and a temperature of 140° C., the feed being at a rate such as to maintain the liquid level in the rection tower 5 at a constant level. In the meantime, compressed air was blown in from a gas inlet 2 at the rate of 1.4 cubic meters per hour (calculated under standard conditions), thus carrying out the continuous oxidation reaction. A reaction mixture of a cyclohexanone concentration of 0.65 mol per liter, a cyclohexauol concentration of 0.37 mol per liter, a cyclohexylhydroperoxide concentration of 0.13 mol per liter a concentration of the total carboxyl groups of 1.33 gram equivalents per liter, and containing 0.1% by weight of water was withdrawn at the rate of 18.3 liters per hour and introduced to an extraction tower 9 maintained at a pressure of 7 kg/cm$^2$ gauge and a temperature of 80° C. In the extraction tower 9 the reaction mixture was brought into contact with an aqueous solution of carboxylic acids which was being circulated at the rate of 3 liters per hour, the concentration of the total carboxyl groups of the aqueous solution under steady operating conditions was 5.1 gram equivalents per litr. While feeding water at the rate of 0.57 liter per hour via line 10, an extraction phase whose concentration of total carboxyl groups under steady operating conditions was 5.1 gram equivalents per liter was withdrawn via line 12 in an hourly amount equal to the amount of water fed via line 10. On the other hand, the liquid extraction residue was returned via lines 8 and 4 to the reaction tower 5, while the gas leaving the reaction tower 5 was cooled at a cooler-condenser 16 and separated into an exhaust gas and a condensed liquid. The exhaust gas was discharged via line 3, while the condensed liquid was conducted to a separator via line 17. The water separated into a lower layer at the separator 15 was discharged via line 6, and the upper layered cyclohexane was returned via line 4 to the reaction tower 5.

By operating in this manner, the concentration of the total carboxyl groups in the liquid extraction residue under steady operating conditions becomes 1.05 gram equivalents per liter, and when the extraction phase withdrawn from line 12 was analyzed, the rates of selectivity for epsilon-hydroxycaproic acid, adipic acid and delta-formylvaleric acid were 34%, 29% and 2%, respectively.

CONTROL I

Example I was repeated except that water was fed via line 10 at the rate of 9.2 liters per hour and the recycling of the extraction phase by means of a pump was not performed but the extraction phase was completely withdrawn from line 12. By operating in this manner, the results shown in FIG. 2 were obtained. The concentration of the total carboxyl groups of the extraction phase withdrawn from line 12 was 0.36 gram equivalent per liter under steady operating conditions in this case.

EXAMPLE II

The continuous oxidation reaction was carried out by feeding cyclohexane via line 1 to an 11-liter stainless steel bubbling column type reaction tower 5 maintained at a pressure of 7 kg/cm$^2$ gauge and a temperature of 140° C., the feed being at a rate such as to maintain the liquid level in the reaction tower 5 at a constant level. In the meantime, compressed air was blown in from a gas inlet 2 at the rate of 1.49 cubic meters per hour (calculated under standard conditions). A reaction mixture of a cyclohexanone concentration of 0.6 mol per liter, a cyclohexanol concentration of 0.35 mol per liter, a cyclohexphydroperoxide concentration of 0.10 mol per liter, a concentration of the total carboxyl groups of 0.63 gram equivalent per liter, and containing 0.1% by weight of water was withdrawn at the rate of 18.3 liters per hour via line 7 and introduced to a first extractor 9 maintained at a pressure of 7 kg/cm$^2$ gauge and a temperature of 80° C., where the reaction mixture was brought into contact with an aqueous solution of carboxylic acids which was being circulated at the rate of 18.3 liters per hour by means of a pump 13, the concentration of the total carboxyl groups of the aqueous solution under steady operation conditions being 6.45 gram equivalents per liter.

Fresh water was fed at the rate of 0.1 liter per hour via line 10 and a liquid extract in an amount equalling the amount of water fed was withdrawn via line 12. The liquid extraction residue was conducted to a second extractor similar to the extractor 9. At the second extractor the liquid extraction residue was brought into contact with an aqueous solution of carboxylic acids which was being circulated at the rate of 12 liters per hour, the concentration of the total carboxyl groups of which aqueous solution was 0.33 gram equivalent per liter under steady operating conditions. The liquid extraction residue was then returned to the reaction tower 5. Further, fresh water was fed to the second extraction tower at the rate of 4.3 liters per hour, and a liquid extract of a concentration of the total carboxyl groups of 0.33 gram equivalent per liter was withdrawn in an amount equalling the amount of water fed.

The exhaust gas from the oxidation tower was treated as in Example I.

By operating in this manner, the concentration of the total carboxyl groups of the liquid extraction residue was maintained at 0.35 gram equivalent per liter. When the extracts obtained from the first and second extraction tower were analyzed, the rates of selectivity for epsilon-hydroxycaproic acid, adipic acid and deltaformylvaleric acid were 35%, 32%, respectively.

EXAMPLE III

Example II was repeated except that 1,6-hexanediol was fed to the first extraction tower at the rate of 0.6 liter per hour and circulated therein at the rate of 4 liters per hour, while a 1.6-hexanediol layer containing carboxylic acids and esters was withdrawn in an amount equalling the amount of 1,6-hexanediol fed. On the other hand, water was fed to the second extraction tower at the rate of 0.3 liter per hour and circulated therein at the rate of 18.3 liters per hour, while a liquid extract in an amount equalling the amount of water fed was withdrawn. By operating in this manner, the concentration of the total carboxyl groups in the liquid extraction residue under steady operating conditions was maintained at 0,3 gram equivalent per liter. The rates of selectivity for epsilon-hydroxycaproic acid, adipic acid and delta-formylvaleric acid were 35%, 33% and 4%, respectively.

EXAMPLE IV

Example III was repeated except that 1,6-hexanediol containing 25% by weight of water was fed to the first extraction tower instead of 1,6-hexanediol. By operating in this manner, the concentration of the total carboxyl groups of the liquid extraction residue under steady operating conditions was maintained at 0.37 gram equivalent per liter, and the rates of selectivity for epsilon-hydroxycaproic acid, adipic acid and deltaformylvaleric acid were 35%, 32% and 3%, respectively.

EXAMPLE V

Example I was repeated except that the liquid extraction residue coming out from the extraction tower 9 was withdrawn at the rate of 0.5 liter per hour from an intermediate point in line 8 while the remainder was returned to the reaction tower 5.

The concentration of the total carboxyl groups of the liquid extraction residue was maintained under steady operating conditions at 0.6 gram equivalent per liter by operating as hereinabove described, and as a result the rates of selectivity for epsilon-hydrox/caproic acid, adipic acid and delta-formylvaleric acid were 36%, 29% and 2%, respectively.

Figure 3:
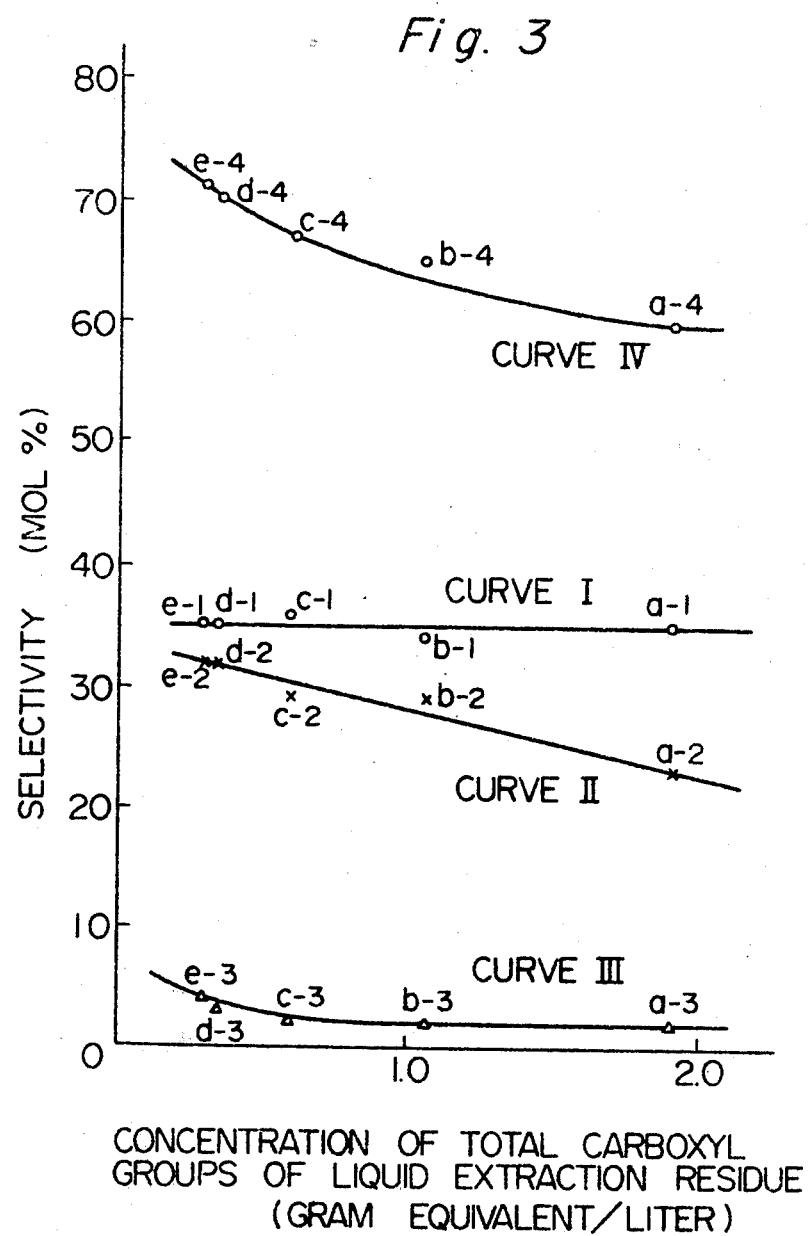

The results obtained in the foregoing Examples I, II, III, V and Control I are shown in the accompanying FIG. 3. In FIG. 3 the ordinate is the selectivity for each of the compounds of epsilon-hydroxycaproic acid, adipic acid and delta-formylvaleric acid as well as the total of the three compounds, while the abscisca is the concentration of the total carboxyl groups of the liquid extraction residue (gram equivalents per liter of the liquid extraction residue). The curves I, II and III represent the rates of selectivity for adipic acid, epsilon-hydroxycaproic acid and delta-formylvaleric acid, respectively, while curve IV represent the total selectivity for the three compounds. On the other hand, the points $a$-1, to $a$-4 are the results of Control I, as plotted on the graph, while points $b$-1 to $b$-4 are those of Example I, points $c$-1 to $c$-4 are those of Example V, points $d$-1 to $d$-4 are those of Example II and points $e$-1 to $e$4 are those of Example III, as plotted on the graph.

As is apparent from FIG. 3, it is seen that the total selectivity for epsilon-hydroxycaproic acid, adipic acid and delta-formylvaleric acid declines when the concentration of the total carboxyl groups of the liquid extraction residue becomes greater than 0.7 gram equivalent, and particular greater than 1.2 gram equivalents.

Experiment B

These experiments were carried out by the batchwise reaction method for investigating the effects of the water content and conversion rate on the selectivity for epsilon-hydroxycaproic acid, adipic acid and delta-formylvaleric acid.

EXAMPLE VI

Effect of Water

A stainless steel 0.7-liter autoclave equipped with an agitator, a gas blow-in line and a reflux condenser was charged with 237 grams of cyclohexane, 12.5 grams of cyclohexanone, 0.41 gram of di-tert. -butyl peroxide and water in an amount indicated in the following table, following which the reaction was carried out for 3 hours at a reaction pressure of 10 kg/cm² gauge and a temperature of 130° C. while blowing in air at the rate of 0.8 liter per hour (calculated at standard conditions). The results obtained are shown in Table 2, below.

Table 2

| Experiment No. | Reaction Temperature (° C.) | Water Content (wt. %) | Conversion (mol %) | Selectivity (mol %) | | | |
|---|---|---|---|---|---|---|---|
| | | | | ε-Hydroxy-caproic acid (I) | Adipic acid (II) | δ-Formyl-valeric acid (III) | (I)+(II)+(III) |
| 1-1 | 130 | 0.5 | 2.7 | 30.0 | 33.2 | 5.4 | 68.6 |
| 1-2 | 130 | 1.5 | 2.3 | 22.1 | 32.5 | 5.8 | 60.4 |
| 1-3 | 130 | 2.5 | 1.8 | 16.0 | 33.3 | 6.3 | 55.6 |

EXAMPLE VII

Effect of Conversion Rate

An autoclave identical to that used in Example VI was charged with 237 grams of cyclohexane, 12.5 grams of cyclohexanone and 0.41 gram of di-tert. -butyl peroxide following which the reaction was carried out at the temperature indicated in the following table until the conversion indicated therein was reached. The results thus obtained are shown in Table 3, below.

Table 3

| Experiment No. | Reaction Temperature (°C.) | Conversion (mol %) | ε-Hydroxy-caproic acid (I) | Adipic acid (II) | δ-Formyl-valeric acid (III) | (I)+(II)+(III) |
|---|---|---|---|---|---|---|
| 2-1 | 130 | 0.32 | 43.6 | 26.2 | 10.0 | 79.8 |
| 2-2 | 130 | 0.46 | 45.6 | 26.5 | 9.1 | 81.2 |
| 2-3 | 130 | 0.6 | 43.2 | 26.5 | 8.0 | 77.7 |
| 2-4 | 130 | 0.91 | 40.7 | 27.0 | 7.1 | 74.8 |
| 2-5 | 130 | 1.50 | 41.7 | 27.8 | 5.5 | 75.0 |
| 2-6 | 130 | 2.5 | 36.3 | 28.5 | 4.2 | 69.0 |
| 2-7 | 130 | 5.0 | 35.0 | 29.0 | 2.5 | 66.5 |
| 2-8 | 140 | 1.8 | 37.5 | 27.5 | 5.0 | 70.0 |
| 2-9 | 140 | 1.0 | 38.5 | 28.0 | 6.5 | 73.0 |

As is apparent from the results of Examples VI and VII given above, it can be seen that the oxidation reaction should preferably be carried out in such a manner that the water content is below 1% by weight and that the conversion of cyclohexane does not exceed 4.5 mol %.

We claim:

1. In a process for preparing a mixture of organic carboxylic acids and esters thereof consisting predominantly of epsilon-hydroxycaproic acid, adipic acid, formylvaleric acid and esters of these acids which comprises oxidizing a mixture of cyclohexane, cyclohexanol, and cyclohexanone with molecular oxygen with the conversion of cyclohexane not exceeding 4.5 mole %, withdrawing the oxidation reaction mixture from the oxidation reaction system, extracting the organic carboxylic acids and esters thereof from the oxidation reaction mixture, recycling to the oxidation reaction system the resulting liquid extraction residue containing unreacted cyclohexane, cyclohexanol and cyclohexanone together with a fresh mixture of cyclohexane, cyclohexanol and cyclohexanone, and carrying out said oxidation reaction while recovering said carboxylic acids and esters thereof from the liquid extract: the improvement wherein said extraction is carried out by contacting said oxidation reaction mixture with an aqueous solution containing the organic carboxylic acids and esters thereof, which are formed by said oxidation reaction, in an amount of 4 gram equivalents to 7 gram equivalents as total carboxyl groups per liter of said aqueous solution, thereby reducing the total concentration of the carboxyl groups of said extraction residue to a value not greater than 0.7 gram equivalent per liter of the extraction residue, with the proviso that the bonds of the esters contained in the extraction residue are regarded as carboxyl groups.

2. The process of claim 1 wherein, in extracting said organic carboxylic acids and esters thereof from the oxidation reaction mixture formed by oxidizing a liquid mixture of cyclohexane, cyclohexanol and cyclohexanone with molecular oxygen, said oxidation reaction mixture is contacted during at least one period of the extraction treatment with an aqueous solution containing the organic carboxylic acids and esters thereof that are formed by said oxidation reaction, in terms of the concentration of total carboxyl groups, in an amount of 4 gram equivalents to 7 gram equivalents per liter of said solution, the several ester bonds being regarded as carboxyl groups.

3. The process of claim 1, wherein, in extracting the organic carboxylic acids and esters thereof from the oxidation reaction mixture formed by oxidizing a liquid mixture of cyclohexane, cyclohexanol and cyclohexanone with molecular oxygen, said oxidation reaction mixture is contacted with a member selected from the group consisting of water and an aqueous solution containing said organic carboxylic acids, esters thereof, or mixture thereof, in terms of the total carboxyl groups, in an amount of 4 gram equivalents to 7 gram equivalents per liter of the solution, withdrawing at least a part of the resulting liquid extraction residue externally of the oxidation reaction system, while recycling the remainder of the liquid extraction residue to the oxidation reaction system.

4. The process of claim 1 wherein the extraction of the organic carboxylic acids and esters thereof from the oxidation reaction mixture formed by oxidizing a liquid mixture of cyclohexane, cyclohexanol and cyclohexanone with molecular oxygen is carried out by contacting said oxidation reaction mixture with at least one glycol selected from the group consisting of 1,2-propanediol, 1,4-butanediol, 1,5-pentanedial, 1,6-hexanediol and diethylene glycol.

5. The process of claim 1 wherein said liquid mixture of cyclohexane, cyclohexanol and cyclohexanone is oxidized by being contacted with a member selected from the group consisting of molecular oxygen or a molecular oxygen-containing gas at a temperature in the range of 120°–150° C and a pressure in the range of 3–30 atmospheres.

* * * * *

UNITED STATES PATENT AND TRADEMARK OFFICE
CERTIFICATE OF CORRECTION

PATENT NO. : 3,991,099
DATED : November 9, 1976
INVENTOR(S) : FUJITA, ET AL.

It is certified that error appears in the above-identified patent and that said Letters Patent are hereby corrected as shown below:

Claim 4, line 8, delete "1,5-pentanedial", insert

-- 1,5-pentanediol --

Signed and Sealed this

Twenty-second Day of February 1977

[SEAL]

Attest:

RUTH C. MASON
*Attesting Officer*

C. MARSHALL DANN
*Commissioner of Patents and Trademarks*